United States Patent [19]

Robert

[11] 4,061,742

[45] Dec. 6, 1977

[54] METHOD OF REDUCING THE UNDESIRABLE GASTROINTESTINAL EFFECTS OF PROSTAGLANDIN SYNTHETASE INHIBITORS WITH PGA COMPOUNDS

[75] Inventor: André Robert, Kalamazoo, Mich.

[73] Assignee: The Upjohn Company, Kalamazoo, Mich.

[21] Appl. No.: 712,437

[22] Filed: Aug. 9, 1976

Related U.S. Application Data

[63] Continuation of Ser. No. 437,444, Jan. 28, 1974, abandoned.

[51] Int. Cl.$^2$ .................. A61K 31/61; A61K 31/215; A61K 31/19
[52] U.S. Cl. ............................... 424/234; 424/273 P; 424/274; 424/305; 424/317

[58] Field of Search ............... 424/234, 273, 274, 305, 424/317

[56] References Cited

U.S. PATENT DOCUMENTS 3,927,213  2/1976  Lippmann ........................... 424/317

*Primary Examiner*—Sam Rosen
*Attorney, Agent, or Firm*—Gabriel Lopez; Sidney B. Williams, Jr.

[57] ABSTRACT

There is disclosed concomitant systemic administration of certain prostaglandins of the PGE-type and PGA-type, for example, 16,16-dimethyl-PGE$_2$ of 16,16-dimethyl-PGA$_2$, and a prostaglandin synthetase inhibitor, for example, indomethacin, aspirin, or phenylbutazone, to mammals, including humans. Thereby the undesirable gastrointestinal effects of the synthetase inhibitor are reduced.

3 Claims, No Drawings

METHOD OF REDUCING THE UNDESIRABLE GASTROINTESTINAL EFFECTS OF PROSTAGLANDIN SYNTHETASE INHIBITORS WITH PGA COMPOUNDS

This is a continuation of application Ser. No. 437,444, filed Jan. 28, 1974, now abandoned.

This invention relates to an improvement in a known process of administration of certain medicinal agents to mammals, including humans, to accomplish a desired medicinal result. In particular, this invention relates to an improvement in the process of systemic administration of a prostaglandin synthetase inhibitor to a mammal, said improvement comprising concomitant systemic administration of an amount of a prostaglandin of the following formula, in an amount effective to reduce the undesirable effects of said prostaglandin synthetase inhibitor:

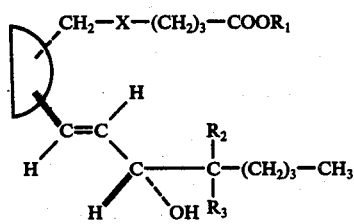

wherein D has the formula:

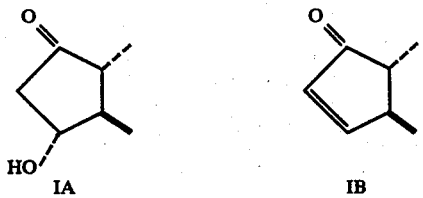

and where $R_1$ is hydrogen, or alkyl of one to eight carbon atoms, inclusive, where $R_2$ is methyl or ethyl, where $R_3$ is hydrogen, methyl or ethyl, and where X is $-CH_2CH_2-$ or cis-CH=CH- or a pharmaceutically acceptable salt thereof when $R_1$ is hydrogen.

According to Takeguchi et al., Prostaglandins, 2, 169 (1972), "Prostaglandin synthetase is a microsomal enzyme complex, which catalyzes the oxidative cyclization of unsaturated $C_{20}$ fatty acids, such as arachidonic acid, into prostaglandins (PG) in the presence of a suitable coenzyme". See also Nugteren et al., Rec. Trav. Chim. Pays-Bas. 85, 405 (1966); Hamberg et al., J. Biol. Chem. 242, 5336 (1967), and Sih et al., J. Am. Chem. Soc. 92, 6670 (1970). This oxidative cyclization is pesently thought to be an in vivo physiological process initiated by one or more physiological mechanisms of as yet unknown nature.

In the case of arachidonic acid (II), this oxidative cyclization is formulated as follows, leading to the prostaglandins known as $PGE_2$ (III) and/or $PGF_{2\alpha}$ (IV).

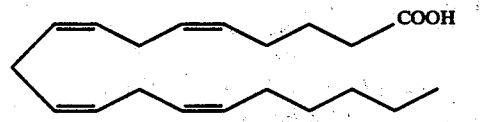

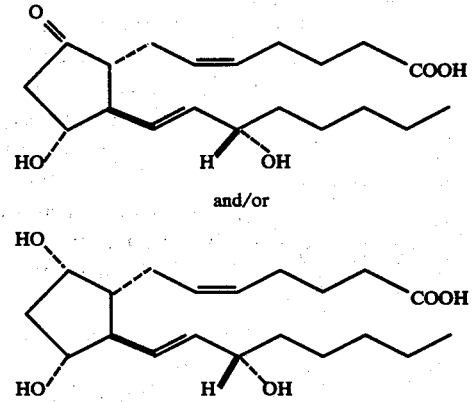

It is now known that certain substances interfere with or inhibit this oxidative cyclization in vitro or in vivo. These substances are referred to broadly as prostaglandin synthetase inhibitors.

It is readily determined in vitro whether or not a particular substance is a prostaglandin synthetase inhibitor. See, for example, Takeguchi et al., above cited.

Many of the substances now known to be prostaglandin synthetase inhibitors are also members of a class known descriptively as non-steroidal anti-inflammatory agents. See, for example, Vane, Nature New Biology, 231, 232 (1971), Takeguchi et al., above cited, and references cited in Takeguchi et al. Included within this class of substances are the well-known anti-inflammatory agents indomethacin, aspirin, and phenylbutazone. Others are mefenamic acid, flufenamic acid, naproxen, 2-phenoxyphenylpropionic acid, (+)-3-chloro-4-cyclohexyl-α-methylphenylacetic acid, and ibuprofen.

It is readily determined in vivo whether or not particular substances, including substances known to be prostaglandin synthetase inhibitors, are anti-inflammatory agents. See, for example, R. A. Turner, "Screening Methods in Pharmacology", Academic Press, New York, Chapter 13, pp. 152-163 (1965), and especially, Winder et al., J. Pharmacol. Exp. Ther. 141, 369 (1963).

It is now well known that administration of certain non-steroidal anti-inflammatory agents, especially by the oral or rectal route, to humans for anti-inflammatory purposes often causes undesirable gastrointestinal effects including but not limited to abdominal pain, single or multiple ulcerations, nodules, adhesions, and other types of lesions, bleeding, anorexia, nausea, and the like. See, for example, Boardman et al., Ann. rheum. Dis. 26, 127 (1967); Taylor et al., Brit. Med. J. 4, 734 (1968); Fischer et al., Am. J. Gastroent. 51, 42 (1969); Sturges et al., Am. J. Gastroent. 59, 162 (1973), Chapman et al., Gut. 10, 443 (1909); Smith, Ann. N.Y. Acad. Sci. 86, 38 (1960); and Gault et al., Ann. Int. Med. 68, 906 (1968). Discontinuing administration of the anti-inflammatory agent usually results in alleviation and later substantially complete relief from these undesirable gastrointestinal effects, especially healing of the ulcers. But meanwhile, the patient has no relief from the inflammatory disease for which he was being treated.

It has been reported that the ulcerogenic effect induced by certain non-steroidal anti-inflammatory agents in rats is inhibited by concomitant oral administration of certain prostaglandins of the E and A series, including PGE$_1$, PGE$_2$, PGE$_3$, 13,14-dihydro-PGE$_1$, and the corresponding 11-deoxy-PGE and PGA compounds. See Partridge et al., U.S. Pat. No. 3,781,429.

I have now made the surprising discovery that certain prostaglandins of the PGE-type and the PGA-type, i.e., those defined by formula I above, are useful in reducing the undesirable gastrointestinal effects resulting from systemic administration of anti-inflammatory prostaglandin synthetase inhibitors, and are used for that purpose by concomitant administration of the formula I PGE-type and PGA-type prostaglandin and the anti-inflammatory prostaglandin synthetase inhibitor. This novel process improvement is useful, for example, in reducing the undesirable gastrointestinal effects resulting from systemic administration of indomethacin, phenylbutazone, and aspirin. These are substances specifically mentioned in Partridge et al. as non-steroidal anti-inflammatory agents. But these are also known to be prostaglandin synthetase inhibitors. The novel process improvement of this invention is useful only in reducing undesirable gastrointestinal effects caused by anti-inflammatory agents which are also prostaglandin synthetase inhibitors. Undesirable gastrointestinal effects caused by anti-inflammatory agents which are not prostaglandin synthetase inhibitors are not expected to be reduced by concomitant administration of a formula I PGE-type or PGA-type prostaglandin.

Prostaglandins may be considered as derivatives of a parent substance known as prostanoic acid, having the following formula and atom numbering

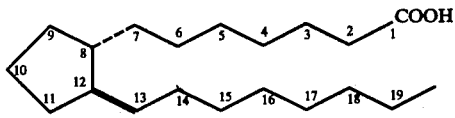

V

The prostaglandin known as PGE$_1$ has the formula:

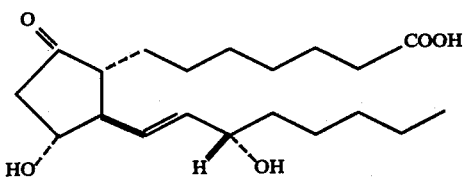

VI

Prostaglandin A$_1$ (PGA$_1$) has the formula:

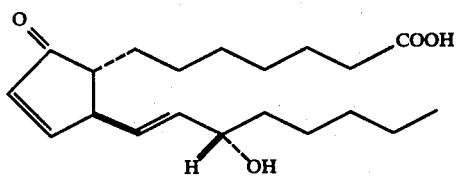

VII

Prostaglandin E$_2$ (PGE$_2$) has the formula:

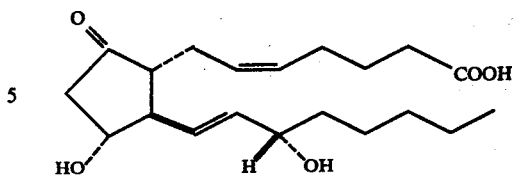

III

Prostaglandin A$_2$ (PGA$_2$) has the formula:

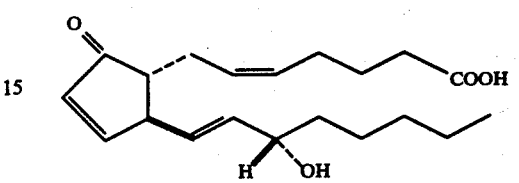

VIII

Thus, it will be seen that formula I, above, encompasses both PGE-type compounds (partial formula IA) and PGA-type compounds (partial formula IB), and that formula I also encompasses PG$_1$-type compounds (X is -CH$_2$CH$_2$-) and PG$_2$-type compounds (X is cis-CH=CH-). Formula I also includes the free acid form, alkyl esters containing one to 8 carbon atoms, inclusive, in the alkyl portion, and pharmaceutically acceptable salts when R$_1$ is hydrogen. These compounds of formula I are known in the art. See, for example, German Offenlegungschrift Nos. 2,210,697 and 2,217,044.

It will be seen that each of the prostaglandin analogs encompassed by formula I differs from PGE$_1$, PGA$_1$, PGE$_2$, or PGA$_2$ in having one or two methyl or ethyl groups at C-16 rather than hydrogen. Thus, in formula I, when D is IA, X is -CH$_2$CH$_2$-, R$_1$ is hydrogen, and R$_2$ and R$_3$ are both methyl, the compound defined is named 16,16-dimethyl-PGE$_1$. When D is IB, X is -CH$_2$CH$_2$-, R$_1$ is hydrogen, and R$_2$ and R$_3$ are both methyl, the compound defined is 16,16-dimethyl-PGA$_1$. Similarly, when X is cis-CH=CH-, R$_1$ is hydrogen, and R$_2$ and R$_3$ are both methyl, the two compounds described are 16,16-dimethyl-PGE$_2$(IA) and 16,16-dimethyl-PGA$_2$ (IB).

These formula I 16-substituted prostaglandins of the PGE-type and the PGA-type are surprisingly and unexpectedly more useful than the corresponding unsubstituted prostaglandins of formulas VI, VII, III, and VIII, including their salts and alkyl esters because the formula I compounds are substantially more potent in the novel process improvement of this invention than said prostaglandins of formulas VI, VII, III, and VIII.

The administration to animals and especially to humans of an anti-inflammatory synthetase inhibitor for treatment of inflammation and related physiological conditions is not by itself part of this invention. Rather, as discussed above, this invention is an improvement in the administration of anti-inflammatory synthetase inhibitors to mammals and especially to humans.

In order to practice this novel improvement, the anti-inflammatory synthetase inhibitor, for example, indomethacin, aspirin, or phenylbutazone, is administered in any of the ways known in the art to alleviate an inflammatory condition, for example, in any dosage regimen and by any of the known routes of systemic administration. It is known, however, that undesirable gastrointestinal effects most often result when the route of administration of the anti-inflammatory substance is oral or rectal, and when relatively large amounts of the substance is administered over a prolonged period of time. It is for such routes of administration and for such dosage regimens that the novel improvement which is this invention is most useful.

The prostaglandin of the formula I PGE-type and PGA-type is administered along with the anti-inflammatory prostaglandin synthetase inhibitor either by the same route of administration or by a different route. For example, if the anti-inflammatory substance is being administered orally, the formula I PGE-type or PGA-type prostaglandin is also administered orally or, alternatively, is administered rectally in the form of a suppository or, in the case of women, vaginally in the form of a suppository or a vaginal device for slow release, for example, as described in U.S. Pat. No. 3,545,439. Alternatively, if the anti-inflammatory substance is being administered rectally, the formula I PGE-type or PGA-type prostaglandin is also administered rectally or, alternatively, orally or, in the case of women, vaginally. It is especially convenient when the administration route is to be the same for both anti-inflammatory substance and prostaglandin, to combine both into a single dosage form.

Dosage forms for both the anti-inflammatory substance and the formula I PGE-type or PGA-type prostaglandin are prepared by methods known in the art. See, for example, Partridge et al., above cited.

Among the formula I PGE-type and PGA-type prostaglandins to be used according to this invention, 16,16-dimethyl-PGE$_2$ and 16,16-dimethyl-PGA$_2$ are especially preferred. Also among the formula I PGE-type and PGA-type prostaglandins, preferred are the free acid forms ($R_1$ is hydrogen), the salt form wherein the cation is pharmaceutically acceptable, and the methyl and ethyl esters ($R_1$ is methyl or ethyl).

This dosage regimen for the formula I PGE-type or PGA-type prostaglandin in accord with this invention will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe and effective amount of the formula I PGE-type or PGA-type prostaglandin to reduce and then substantially to eliminate those undesirable effects. In doing that, the physician or veterinarian would, or course, start at a relatively low concomitant dose of the prostaglandin, for example, about 0.1 µg./kg./day of 16,16-dimethyl-PGE$_2$ or about 0.5 µg./kg./day of 16,16-dimethyl-PGA$_2$, and observe the response of the human or animal patient for a few days. The dose of the formula I PGE-type or PGA-type prostaglandin is then adjusted downward or upward until the minimum effective dose is found. For example, in the case of 16,16-dimethyl-PGE$_2$, the maximum needed dose is usually about 10 µg./kg./day and in the case of 16,16-dimethyl-PGA$_2$, the maximum needed dose is usually about 20 µg./kg./day, although it may be necessary occasionally to exceed these doses when large amounts of the inflammatory substance are needed for a particular medical indication or when the gastrointestinal response of a particular subject to the anti-inflammatory substance is especially severe and there is a sound medical reason for maintaining the subject on that particular anti-inflammatory substance. Once the minimum effective dose of the particular formula I PGE-type or PGA-type compound is determined for a particular subject, it is advantageous to provide the subject with a single dosage form which contains both the desired amount of the anti-inflammatory substance and the amount of the prostaglandin effective to obtain the desired gastrointestinal result.

Since not all animal and human subjects have adverse gastrointestinal responses to administration of an anti-inflammatory prostaglandin synthetase inhibitor, rational medical therapy indicates that the formula I PGE-type or PGA-type compound not be administered until the need for that appears in any particular animal or human subject. But when this need is observed, it can be expected that, at least in some subjects, a higher level of the prostaglandin will be needed along with the anti-inflammatory substance to allow the gastrointestinal tract to return to normal during continued administration of the anti-inflammatory substance than will later be necessary to maintain a normal gastrointestinal tract. It is, however, within the skill of the attending physician or veterinarian to adjust the dose of the formula I PGE-type or PGA-type prostaglandin to meet the needs of the individual human or animal subject especially in the usual situations involving long term regimens of anti-inflammatory substances. In this respect, the term "effective amount" of the prostaglandin will mean amounts effective at various time periods during administration of an anti-inflammatory substance. An amount of the formula I PGE-type or PGA-type substance effective to allow healing of existing gastrointestinal ulcers, for example, will not necessarily be the same and, indeed, is likely to be more than the amount effective to avoid formation of future ulcers. The process improvement which is this invention includes both of these concepts of "effective amount".

I claim:

1. A method of systemic administration of an anti-inflammatory prostaglandin synthetase inhibitor to a mammal, the improvement which comprises concomitant systemic administration of (a) said inhibitor, and (b) a prostaglandin of the following formula

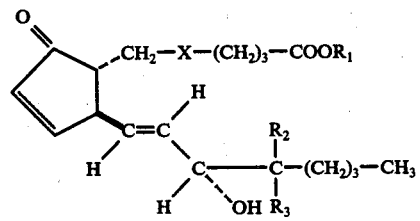

in an amount effective to reduce the gastrointestinal effects of the prostaglandin synthetase inhibitor where $R_1$ is hydrogen, or alkyl of one to 8 carbon atoms, inclusive, where $R_2$ is methyl or ethyl, where $R_3$ is hydrogen, methyl or ethyl, and where X is -CH$_2$CH$_2$- or cis-CH=CH- or a pharmaceutically acceptable salt thereof when $R_1$ is hydrogen.

2. A method of systemic administration of an anti-inflammatory prostaglandin synthetase inhibitor to a mammal, the improvement which comprises concomitant systemic administration of (a) said inhibitor, and (b) a prostaglandin of the following formula

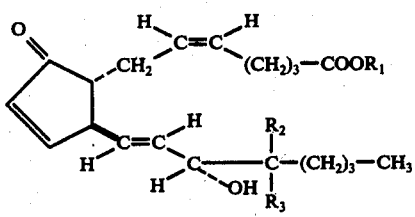

in an amount effective to reduce the gastrointestinal effects of the prostaglandin synthetase inhibitor where $R_1$ is hydrogen, or alkyl of one to 8 carbon atoms, inclusive, where $R_2$ is methyl or ethyl, where $R_3$ is hydrogen, methyl or ethyl, or a pharmaceutically acceptable salt thereof when $R_1$ is hydrogen.

3. A method of systemic administration of an anti-inflammatory prostaglandin synthetase inhibitor to a mammal, the improvement which comprises concomitant systemic administration of (a) said inhibitor, and (b) 16,16-dimethyl-$PGA_2$ including its alkyl esters of one to 8 carbon atoms, inclusive, or a pharmaceutically acceptable salt thereof in an amount effective to reduce the gastrointestinal effects of the prostaglandin synthetase inhibitor.

* * * * *